United States Patent [19]
Sadoway et al.

[11] Patent Number: 5,489,849
[45] Date of Patent: Feb. 6, 1996

[54] HIGH ACCURACY CALIBRATION-FREE ELECTRICAL PARAMETER MEASUREMENTS USING DIFFERENTIAL MEASUREMENT WITH RESPECT TO IMMERSION DEPTH

[75] Inventors: Donald R. Sadoway, Belmont; Kevin G. Rhoads, Andover; Naomi A. Fried, Cambridge; Susan L. Schiefelbein, Boston, all of Mass.

[73] Assignee: Massachusetts Institute of Technology, Cambridge, Mass.

[21] Appl. No.: 212,478

[22] Filed: Mar. 14, 1994

[51] Int. Cl.$^6$ .................................................. G01N 27/02
[52] U.S. Cl. ........................ 324/447; 324/449; 204/406; 205/81
[58] Field of Search ............................ 324/444, 446, 324/447, 448, 449, 720, 691; 204/406; 205/81–83

[56] References Cited

U.S. PATENT DOCUMENTS

| | | | |
|---|---|---|---|
| 2,082,213 | 6/1937 | O'Donnell | 175/183 |
| 2,221,307 | 11/1940 | Christie | 175/183 |
| 2,898,549 | 8/1959 | Miller | 324/30 |
| 3,047,797 | 7/1962 | Borsboom | 324/30 |
| 3,218,552 | 11/1965 | Asmann et al. | 324/65 |
| 3,320,529 | 5/1967 | Vreeland et al. | 324/62 |
| 4,118,663 | 10/1978 | Barben, II | 324/443 |
| 4,767,995 | 8/1988 | Berry, Jr. | 324/447 |
| 4,780,663 | 10/1988 | Mulder | 324/65 |
| 5,025,219 | 6/1991 | Gaspard | 324/447 |
| 5,089,780 | 2/1992 | Megerle | 324/448 |

OTHER PUBLICATIONS

Kim, Kwang Bum, et al., "Electrical Conductivity Measurements of Molten Alkaline–Earth Fluorides," *J. Electrochem. Soc.*, 139(4):1027–1033, (Apr. 1992).

Wu, Y. C., et al., "Review of Electrolytic Conductance Standards," *Journal of Solution Chemistry*, 16(12):985–997, (Nov. 1987).

Jones, Grinnell, et al., "The Measurement of the Conductance of Electrolytes. III. The Design of Cells," *Journal of the American Chemical Society*, pp. 411–419, (Feb. 1931).

Bard, A. J., et al., *Electrochemical Methods: Fundamentals and Applications*, John Wiley & Sons, pp. 316–369. Date unavailable.

Macdonald, J. R., et al., *Impedance Spectroscopy—Emphasizing Solid Materials and Systems*, John Wiley & Sons, pp. 1–29. Date unavailable.

Thomas, J. L., "Precision Resistors and Their Measurements," National Bureau of Standards Circular 470, Issued Oct. 8, 1948.

(List continued on next page.)

*Primary Examiner*—Kenneth A. Wieder
*Assistant Examiner*—Christopher M. Tobin
*Attorney, Agent, or Firm*—Hamilton, Brook, Smith & Reynolds

[57] ABSTRACT

An apparatus and method for measuring electrical parameters of a medium such as electrical conductivity and dielectric constant between a pair of electrodes are disclosed. The medium can be a liquid, gas, powder, etc., and the electrodes can be coaxial metallic circular cylinders. To compute electrical conductivity, the device is immersed in the medium to an immersion depth and the conductance across the electrodes is determined. The measurement is repeated at at least one additional immersion depth. By obtaining a differential conductance measurement with respect to the immersion depth, the effects of fringe conductances are eliminated from the measurement. The device can also be used to determine dielectric constant of the material by obtaining a differential capacitance measurement with respect to immersion depth. The device need not be calibrated by performing resistance measurements in a known standard solution. Also, because the electrodes can be purely metallic and include no dielectric material, the device can be used to perform measurements in highly corrosive media whose compositions would be altered upon contact with dielectric materials.

31 Claims, 5 Drawing Sheets

OTHER PUBLICATIONS

Kissinger, P. T., et al., *Laboratory Techniques in Electroanalytical Chemistry*, Marcel Dekker, Inc. (1984), pp. 242–266. Month unavailable.

Plambeck, J. A., *Electroanalytical Chemistry*, John Wiley & Sons (1982), pp. 96–99. Month unavailable.

Pungor, E., *Oscillometry and Conductometry, Pergamon Press* (1965), pp. 18–19 and 53–63. Month unavailable.

Janz, G. J., *Molten Salts Handbook, Academic Press* (1967), pp. 499–500. Month unavailable.

Nichol et al., "A New Cell Design for Precision Conductimetry," *J. Phys. Chem.* (1954), pp. 696–699. Month unavailable.

Mills, K. C., et al., "The Physicochemical Properties of Slags," National Physical Laboratory Report Chem 103, pp. 1–51, (Nov. 1979).

Ohta, Y., et al., "Study on the measuring method of the electrical conductivity of ionic solutions and melts," *Japan Inst. Met.*, 45(10):1036–1043, (1981). English–language translation enclosed. Month unavailable.

Silny, a., et al., "Electrical conductivity measurements of corrosive liquids at high temperatures," *Rev. Sci Instrum.*, 64(2):532–537, (Feb. 1993).

Sheppard, N. F., Jr., et al., "Electrical Conductivity Electrodes," *Analytical Chemistry*, 65(9):1199–1202, (May 1993).

Verevkin, V. I., et al., "Installations for Measuring the Electrical Conductivity of Melts," *Industrial Laboratory—USSR*, 57(1):53–56, (1991). Month unavailable.

Buckel, E. R., et al., "The Accurate Measurement of Electrolytic Conductance in Ionic Melts," *J. Chem. Soc.*, pp. 667–676, (1964). Month unavailable.

Boiko, V. P., et al., "A Cell to Measure the Electrical Conductivity of Solutions," *Instruments and Experimental Techniques*, 35(4):725–727, (1992). Month unavailable.

Kurochkin, B. V., "A New Differential Method of Measuring Liquid Electrical Conductivity," *Measurements Techniques USSR*, 33(4):413–416, (1990). Month unavailable.

Byalo, V. D., et al., "Systematic Errors in the Measurements of Electrical Conductivity of Slag Melts and Ways of Reducing Them," *Industrial Laboratory*, 59(1):31–38, (1993). Month unavailable.

Baucke, F. G., et al., "Accurate conductivity cell for molten glasses and salts," *Glastech. Ber.*, 62(4):122–126, (1989). Month unavailable.

HIGH ACCURACY CALIBRATION-FREE ELECTRICAL PARAMETER MEASUREMENTS USING DIFFERENTIAL MEASUREMENT WITH RESPECT TO IMMERSION DEPTH

GOVERNMENT FUNDING

This invention was made with government suppport under Contract Number N00014-90-J-1721 awarded by the Department of the Navy. The government has certain rights in the invention.

BACKGROUND OF THE INVENTION

In industrial processes such as electroplating, electropolishing and anodizing, and in many other applications, electrical parameters such as the electrical conductivity and dielectric constant of certain fluids have a substantial impact. In such industries and applications, real-time monitoring of the fluid's electrical parameters can be of significant importance.

Many devices and methods have been developed for measuring the electrical conductivity of fluids. Some methods involve immersing a pair of electrodes in the fluid and measuring the resistance, or alternatively the conductance, between the electrodes. The measured resistance across the electrodes is proportional to the electrical resistivity of the fluid with which they are in contact. The proportionality factor, called the cell constant, is theoretically derivable from the geometry of the electrode configuration, with possible geometries including pairs of parallel plates, side-by-side cylindrical electrodes, and coaxial cylindrical electrodes. The known proportionality factor combined with the measured resistance or conductance yields a determination of the electrical conductivity of the fluid.

Typically, the prior devices measure electrical conductivity by first calibrating the device with a standard fluid having a known electrical conductivity. By immersing the device in the standard fluid and measuring the resistance across the electrodes, the cell constant of the device is quantified. Thereafter, resistivity measurements can be made on other fluids by immersing the device of presumed known cell constant into the fluid and measuring the resistance across the electrodes. Since the resistance and proportionality factor (cell constant) are known, the electrical conductivity of the fluid is obtained.

This prior approach relies on the premise that the relationship between the electrical conductivity of the fluid and the resistance measured by the device is completely attributable to the geometry of the device, which is presumed not to change and is independent of the fluid in which the device is immersed and the operating conditions of the device. However, it is known that certain fluid-dependent effects, of which this prior calibration procedure does not take account, attend these resistance measurements. Among the effects are fringe current paths which appear electrically in parallel with the normal current paths between the electrodes. These parallel or shunt current paths appear as parallel conductances across the electrodes which, depending upon the fluid, its container and the container surfaces, can have a marked effect on the resistance measurement obtained. That is, since these fringing effects can vary substantially with fluid and measuring conditions, the typical prior calibration-based procedure can have substantial inherent inaccuracies.

In other prior systems, in an effort to precisely control the device geometry or to limit fringe current effects, the conducting electrodes are mounted to, or separated by, dielectric materials. These devices still use the standard fluid calibration procedure, but because of the precise construction, they show improved accuracy. However, they cannot be used to measure electrical conductivity of highly corrosive media since, upon contact with the dielectric, the composition of the medium is altered.

SUMMARY OF THE INVENTION

The present invention is directed to a device and a method for obtaining accurate measurements of electrical parameters such as electrical conductivity and dielectric constant of both corrosive and non-corrosive media including fluids (for example, liquids, aqueous solutions and gases), solids (for example, powders) and mixtures of fluids and solids (for example, slurries), without the need for calibrating the device in a known-parameter medium. The description of the invention contained herein refers to the invention as determining electrical conductivity of the medium from conductance or resistance measurements. However, as will be described below, the description applies also to determining electrical parameters such as dielectric constant from capacitance measurements. Also, the description contains references to measuring electrical parameters of liquids. It will be understood that the invention is applicable to many types of media including those listed above.

An effective cell constant of the device is computed directly from its geometry and therefore the device can be used for measurements in any medium regardless of its electrical conductivity. The electrical conductivity measurement is obtained by immersing the electrodes of the device in the medium at more than one depth and measuring the impedance of the system at each depth. Since the fringe effects are constant with depth, the plural measurements together with the data analysis of the invention, based on an equivalent circuit of the cell, eliminate the fringe effects, and an accurate electrical conductivity measurement is obtained.

In one embodiment, the device comprises a pair of metallic conductive coaxial circular cylindrical electrodes. The cell constant of such a device is determined by the radii of the cylinders and the cell length, which for purposes of the invention is the depth to which the cylinders are immersed in the medium. Varying the immersion depth of the cell within the liquid effectively varies the cell length, and so the cell constant varies with immersion depth. Since the cell constant is a function of the reciprocal of the cell length, the reciprocal of the cell constant is a linear function of immersion depth, and the variation in reciprocal cell constant with immersion depth, the effective cell constant, is a constant determined only by the radii of the individual cylindrical electrodes.

As stated above, the resistance between the electrodes is simply the product of the cell constant and the resistivity of the medium. Therefore, the reciprocal of resistance, conductance, is the product of the reciprocal of the cell constant and the reciprocal of resistivity, electrical conductivity, of the medium between the electrodes. By taking multiple conductance measurements at multiple immersion depths, a relationship between conductance and immersion depth is obtained. The differential of conductance with respect to immersion depth is equal to the product of the electrical conductivity of the medium and the differential of the reciprocal cell constant with respect to immersion depth, which, as stated above, is a constant. The electrical conductivity of the medium is therefore completely characterized by the measured differential conductance with respect to immersion depth and the known reciprocal cell constant variation with respect to cell length.

Because a differential approach is used, the absolute immersion depth of the cell within the medium need not be determined. It is necessary to know only the differences in immersion depths. This is an important feature in applications where the medium is not accessible to obtain a depth measurement, such as where the parameter measurement is being performed in a high-temperature environment within a closed chamber. Even where the medium is accessible, a measurement of absolute immersion depth is difficult to obtain, especially where the medium is a liquid. The present invention eliminates the need to obtain such an absolute measurement. If the amount of change in immersion depth between measurements is known, the electrical parameter can be determined.

In the above outlined procedure, the conductance measurements inherently include fringe conductance effects. However, from field theory it is known that as long as the medium is uniform, the fringe effects will be constant with immersion depth. Therefore, computation of the differential conductance with respect to immersion depth eliminates the constant fringe conductance from the result, yielding a highly accurate electrical conductivity measurement.

For purposes of the constant fringe effects assumption, the medium through which the fringes propagate must be uniform. In the present application, this means that the bottom of the cell must not approach the boundary (e.g., the free surface and the container floor) of the medium under investigation. It is also known from field theory that the fringe fields will decay rapidly in an axial direction away from the electrodes. Specifically, at a distance equal to twice the difference in radii of the coaxial cylinders, the fringe fields decay to negligible levels. Therefore, as long as the device is kept beyond that distance from the boundaries of the medium, the constant fringe assumption holds, and the electrical conductivity measurement maintains its accuracy.

Because the fringe effects are eliminated from the measurement, the device of the invention does not require dielectric material where the electrodes contact the medium. Only the metallic electrodes themselves need to be immersed in the medium. This makes the invention applicable to measurements of highly corrosive media such as molten oxides. Prior devices which required dielectric material could not obtain such measurements since, in such devices, the composition of the corrosive medium is altered upon contact with the dielectric material.

The device of the invention obtains its measurements without the need for calibration. This is highly desirable in production environments in which high-speed measurements in real time are required. Also, even in prior systems in which calibration is performed, the accuracy of the present invention cannot be achieved since the prior systems do not compensate for the variation in fringe effects from medium to medium.

In order to both prevent electrochemical reaction and remain within that region of the current-voltage characteristic where linear circuit analysis is either exactly or approximately applicable, a very low ac voltage signal (typically on the order of tens of millivolts) must be used to perturb the medium under investigation. Thus, the invention employs impedance spectroscopy to obtain the measurements. Impedance measurements are taken over a wide frequency range by swept frequency or stepped frequency impedance analysis equipment. In one embodiment, the resistance across the electrodes is taken to be the impedance at which the reactance is a minimum after removal of lead wire parasitics by nulling. This technique takes into account various reactive effects including lead wire and electrode impedances, the capacitance of the medium and the double-layer capacitance at each electrode. Accurate determination of resistance must be made using appropriate means for the medium and conditions being measured. For most media, impedance spectroscopy followed by data analysis using an accurate equivalent circuit model of the measuring system will yield adequate resistance measurements.

The impedance spectroscopy technique also allows the invention to determine the dielectric constant of the medium by measuring capacitance across the electrodes instead of conductance. At some frequency within the frequency range, the resistive or real contribution to the total impedance will equal the reactive or imaginary contribution. At that frequency, the capacitance can readily be determined. The capacitance between the electrodes is related to the dielectric constant of the medium by the same cell constant proportionality factor used to define the relationship between conductance and electrical conductivity at all frequencies provided only that the values intrinsic to cell and medium have been isolated from other circuit component's contributions. Therefore, by performing the same analysis at multiple immersion depths, a differential capacitance with respect to immersion depth is obtained. Combining this with the known differential reciprocal cell constant with respect to cell length yields the dielectric constant of the medium.

BRIEF DESCRIPTION OF THE DRAWINGS

The foregoing and other objects, features and advantages of the invention will be apparent from the following more particular description of preferred embodiments of the invention, as illustrated in the accompanying drawings in which like reference characters refer to the same parts throughout the different views. The drawings are not necessarily to scale, emphasis instead being placed upon illustrating the principles of the invention.

DETAILED DESCRIPTION OF THE INVENTION

Figure 1A:
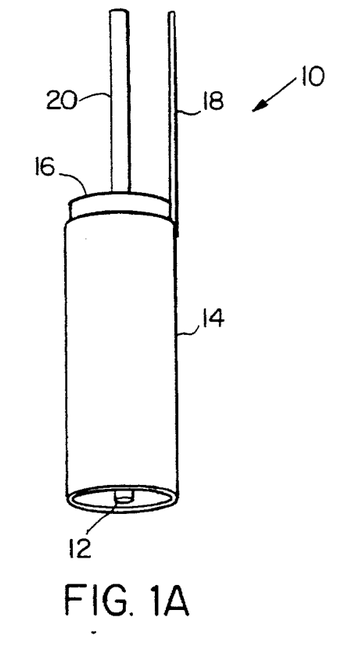
FIG. 1A is a schematic perspective view of an embodiment of the electrical parameter measuring device of the invention.

FIG. 1A is a schematic illustration of a parameter measuring device 10 in accordance with the present invention. The device 10 includes two coaxial circular cylindrical electrodes, an inner electrode 12 within an outer electrode 14. Both electrodes are made of a highly conductive material, typically metal, such as platinum, gold, aluminum or other conductive material. The electrodes 12, 14 are mounted to and separated from each other by a dielectric separator 16. A conductive lead 18 is connected to the outer electrode 14, and a conductive lead 20 is connected to the inner electrode 12. The leads 18, 20 are connected to analysis equipment (not shown) which obtain the impedance measurements between the electrodes 12, 14.

Figure 1B:
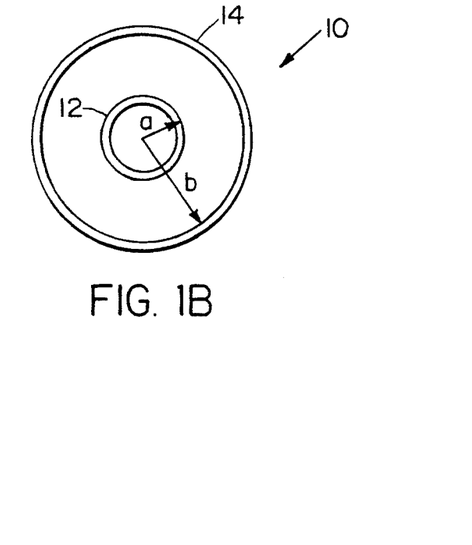
FIG. 1B is an enlarged schematic cross-sectional view of the device of FIG. 1A.

FIG. 1B is an enlarged schematic cross-sectional view of the cell 10 of the invention looking along the longitudinal axes of the electrodes 12, 14. From field theory, the ideal cell constant L of the device 10 is given by $$L = \frac{\ln\left(\frac{b}{a}\right)}{2\pi l} \text{ ; where} \tag{1}$$

b is the inside diameter of the outer electrode 14, a is the outside diameter of the inner electrode 12, and l is the cell length. The cell length l is the depth to which the cell 10 is immersed in the medium whose electrical parameter is being determined. Therefore, l is also referred to herein as the immersion depth. For example, with a liquid medium, l is the wetted length. Note that, especially for relatively small volumes of liquid, the displacement of liquid by the electrodes needs to be accounted for in determining l. The reciprocal cell constant $$\frac{1}{L}$$

is therefore $$\frac{1}{L} = \frac{2\pi l}{\ln\left(\frac{b}{a}\right)}. \tag{2}$$

The variation in $$\frac{1}{L}$$

with respect to immersion depth l is therefore given by $$\frac{d}{dl}\left[\frac{1}{L}\right] = \frac{2\pi}{\ln\left(\frac{b}{a}\right)}. \tag{3}$$

The quantity $$\frac{d}{dl}\left[\frac{1}{L}\right]$$

is called the effective cell constant and is determined completely by the electrode radii a and b and is independent of immersion depth l.

The relationship between resistance R and resistivity ρ is $$R = \rho L. \tag{4}$$

Equivalently, $$\frac{1}{R} = \sigma \left[\frac{1}{L}\right];$$

where $$\frac{1}{R} = G$$

is the conductance between the electrodes, $$\sigma = \frac{1}{\rho}$$

is the electrical conductivity of the material, and L is the cell constant. Therefore, in an ideal cell with no fringe effects, the relationship between the conductance between the electrodes and the electrical conductivity σ of the material is given by $$\frac{1}{R} = \sigma \left[\frac{2\pi l}{\ln\left(\frac{b}{a}\right)}\right] \tag{6}$$

Taking into account the fringe conductances, equation 6 becomes $$\frac{1}{R} = \sigma \left[\frac{2\pi l}{\ln\left(\frac{b}{a}\right)}\right] + \left(\frac{1}{R}\right)_{fringe} \tag{7}$$

The extent of the fringe effect depends on the electrical conductivity of the medium and does not depend on the immersion depth. Therefore, the contribution of the fringe conductance remains constant at all immersion depths (provided the bottom of the electrodes is sufficiently far from boundaries) and differs only from one medium to the next. Recognizing this, a differential approach is used, taking conductance measurements at multiple immersion depths and computing the electrical conductivity of the medium based on the variation in conductance with respect to depth of immersion. Using this differential approach, equation 7 becomes $$\frac{d}{dl}\left[\frac{1}{R}\right] = \sigma \frac{d}{dl}\left[\frac{2\pi l}{\ln\left(\frac{b}{a}\right)}\right] + \frac{d}{dl}\left[\left(\frac{1}{R}\right)_{fringe}\right] = \tag{8}$$

$$\sigma\left[\frac{2\pi}{\ln\left(\frac{b}{a}\right)}\right].$$

Therefore, $$\sigma = \frac{d}{dl}\left[\frac{1}{R}\right]\left[\frac{\ln\left(\frac{b}{a}\right)}{2\pi}\right]. \tag{9}$$

As described above, to obtain the electrical conductivity measurement, conductance measurements are taken at a plurality of immersion depths. That is, at depths $l_0$, $l_1 = (l_0 + \Delta l_1)$, $l_2 = (l_1 + \Delta l_2)$, . . . , —where $l_0$ is an arbitrary initial immersion and $\Delta l_1$ and $\Delta l_2$ are the differences in immersion of the electrodes between immersion 0 and 1, and 1 and 2, respectively-conductance measurements $$\frac{1}{R_0}, \frac{1}{R_1}, \frac{1}{R_2} \ldots,$$

are obtained. To illustrate, where only two measurements are taken, the following are obtained.

$$\frac{1}{R_0} = \sigma \left[ \frac{2\pi l_0}{\ln\left(\frac{b}{a}\right)} \right] + \left(\frac{1}{R}\right)_{fringe} \quad (10)$$

$$\frac{1}{R_1} = \sigma \left[ \frac{2\pi l_1}{\ln\left(\frac{b}{a}\right)} \right] + \left(\frac{1}{R}\right)_{fringe} \quad (11)$$

Equations 10 and 11 can be combined to obtain $$\left[ \frac{1}{R_1} - \frac{1}{R_0} \right] = \sigma \frac{2\pi}{\ln\left(\frac{b}{a}\right)} [\Delta l_1]. \quad (12)$$

The electrical conductivity $\sigma$ can then be computed by $$\sigma = \frac{\ln\left(\frac{b}{a}\right)}{2\pi} \left[ \frac{\frac{1}{R_1} - \frac{1}{R_0}}{\Delta l_1} \right]. \quad (13)$$

From equation 13, it should be noted that the absolute immersion depth need not be known; only the difference in immersion, $\Delta l_1$, need be known.

Figure 2:
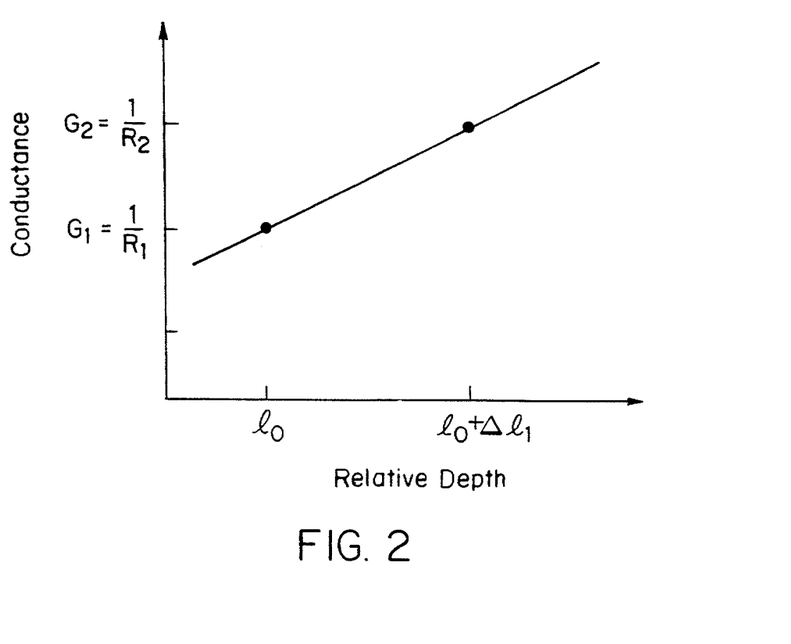
FIG. 2 is a plot of conductance measured by the device of the invention versus relative or differential immersion depth of the device.

FIG. 2 is a graphical representation of the measured conductance $$\frac{1}{R}$$

as a function of differential or relative immersion depth 1. The term in brackets in equation 13 is the slope of the line fitted to the data points. Where only two relative immersion depths $l_1$ and $l_2$ are taken, the line is clearly defined. However, in a preferred embodiment several measurements, preferably four to six, are taken. In that case, a line is fitted to the data points, and the slope of the line is obtained in order to calculate the electrical conductivity $\sigma$ of the medium.

Figure 3A:
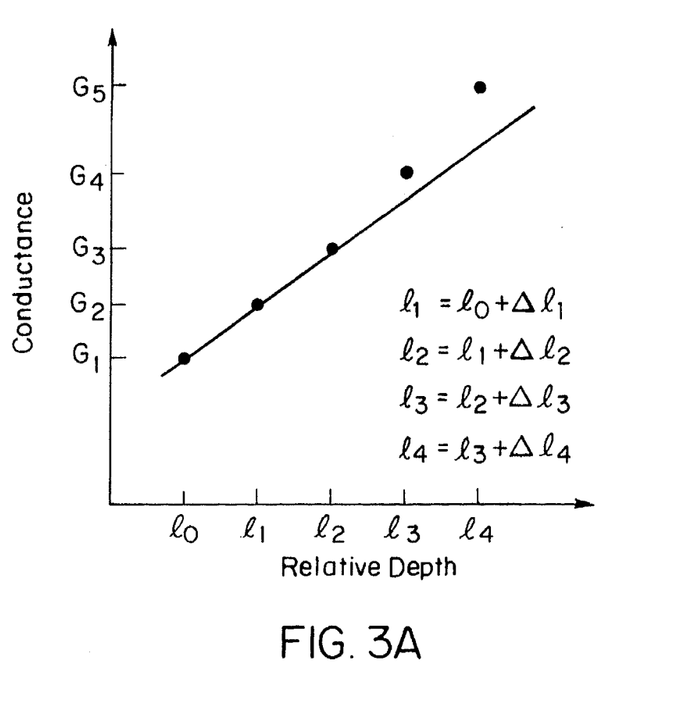
FIGS. 3A and 3B are plots of conductance measured by the device of the invention versus relative immersion depth where the device is positioned too close to the floor of the medium container.
Figure 3B:
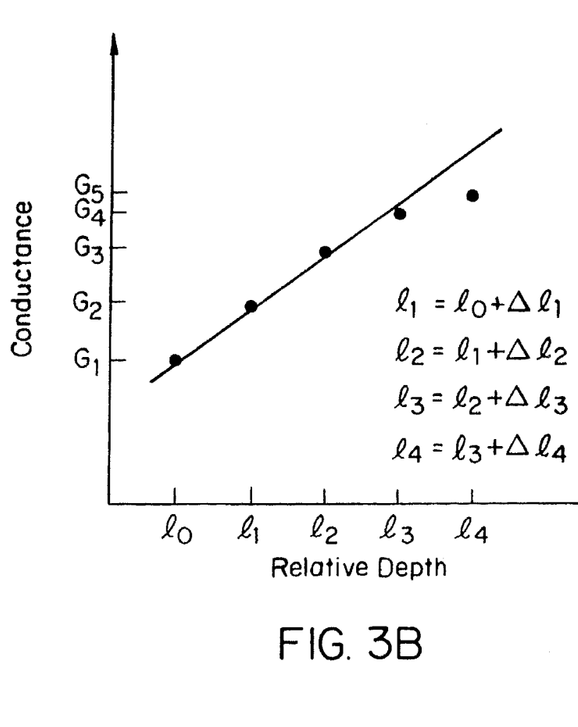

An advantage to using more than two measurements with a graphical display is that it provides a visual check on the correctness of the measurements. The accuracy of this measurement depends upon the fulfillment of the key assumption of the consistency of fringe contribution which results by avoiding too close an approach to the boundaries of the medium under investigation. Should this assumption fail, for example by operator error or equipment failure, the series of points of conductance G or inverse resistance 1/R, plotted against relative depth of immersion 1 will fail to fall along a straight line. This immediate feedback not only indicates erroneous operation, but the form of deviation from a straight line helps diagnose the nature of the error. FIGS. 3A and 3B show the deviation upon too close of an approach to a container floor; for FIG. 3A the container is more conductive than the medium, and for FIG. 3B the container is less conductive.

Figure 4:
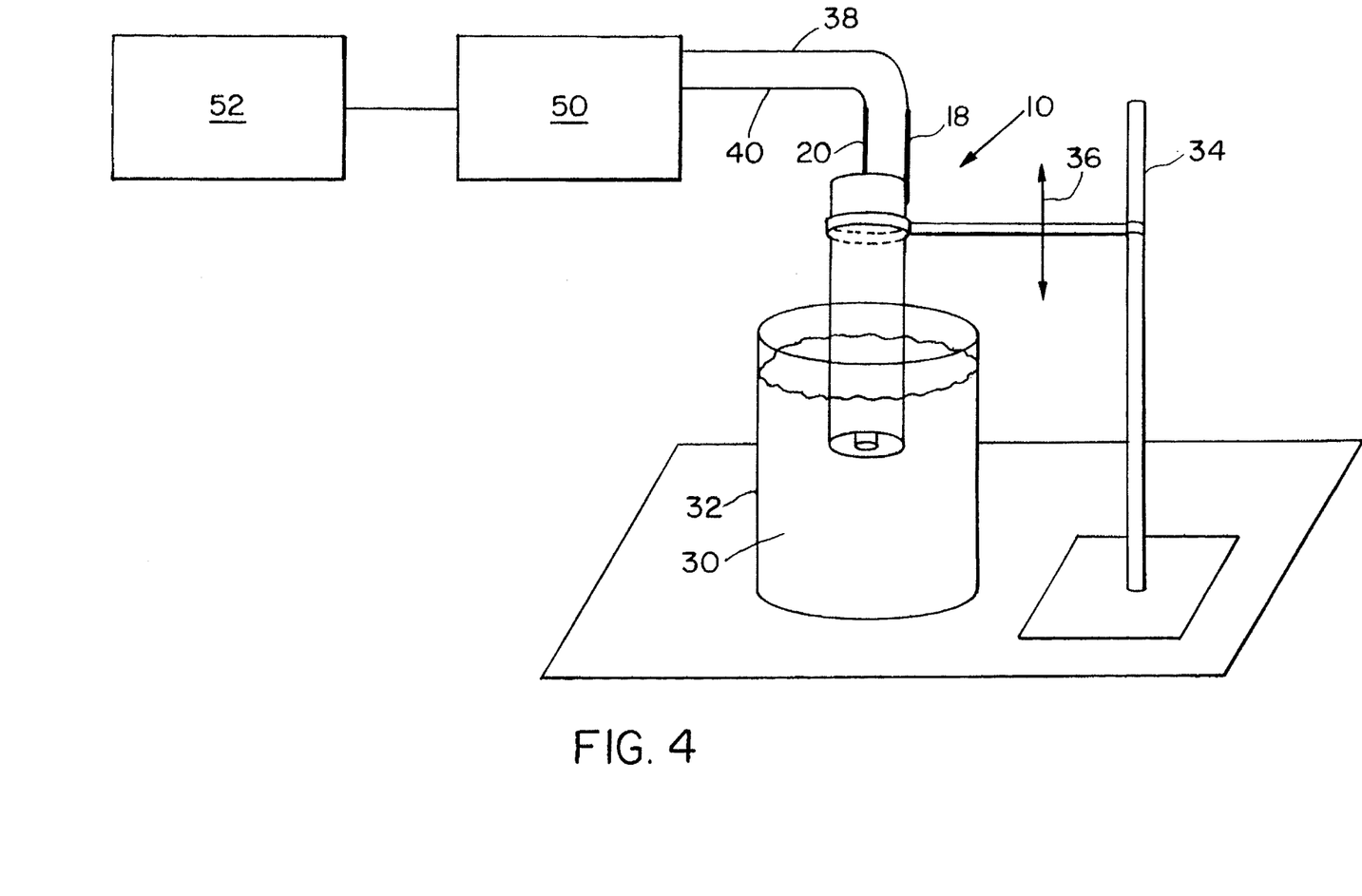
FIG. 4 is a schematic illustration of a system employing the device of the invention to determine electrical conductivity of a liquid.

FIG. 4 is a schematic representation of a system employing the electrical conductivity measuring device 10 of the invention. The cell 10 is shown immersed in a fluid 30 within a container 32. An adjustable support apparatus 34 holds the cell 10 within the container 32. The height of the support is adjustable up and down as indicated by arrow 36 in order to change the immersion depth between measurements. The height of the cell 10 can be precisely controlled by the support 34 such that the differential depths for the measurements can be precisely controlled and determined. It will be understood that the representation of the support apparatus 34 is schematic. It is intended to represent any device which can support the cell 10 of the invention within the material at different immersion depths while permitting a determination of the difference in the various immersion depths.

The electrodes 18 and 20 are connected by a pair of leads 38 and 40, respectively, to analysis equipment 50. The analysis equipment 50 includes an impedance analyzer which provides the impedance measurement between the electrodes over a range of frequencies. For example, the analysis equipment 50 can include an impedance/gain-phase analyzer or a combination of a lock-in amplifier and a variable frequency ac power source, or other similar equipment. The analysis equipment 50 is coupled to a data processor or recorder 52 which receives the impedance measurements from the analyzing equipment 50 to process or record for later analysis the data in accordance with the invention.

Figure 5A:
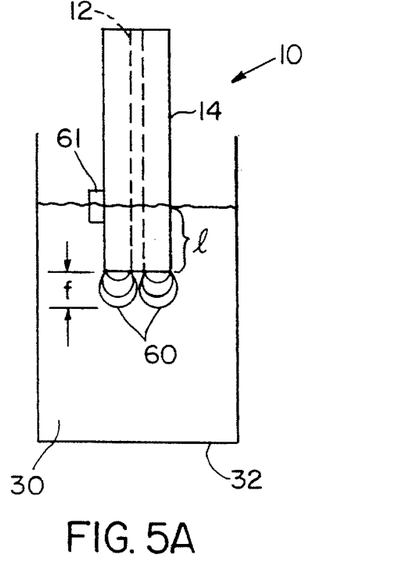
FIG. 5A and 5B are schematic illustrations of the fringe conductances and surface effects of the device of the invention at different relative immersion depths.
Figure 5B:
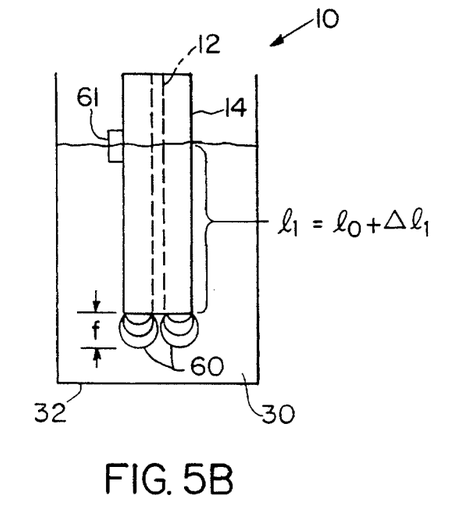

FIGS. 5A and 5B schematically illustrate the electrodes 12, 14 of the cell 10 of the invention immersed to different relative immersion depths $l_1$ and $l_2$ to obtain conductance measurements. The FIGS. also show fringe currents 60 flowing between the electrodes 12, 14, and the consideration of the surface current effects which occur within the brackets 61.

In FIG. 5A, the device 10 is immersed in the medium 30 to an arbitrary initial depth $l_0$. The loops in the fringe current fields 60 indicate parallel current paths between the electrodes which are not normal to the electrodes. The significant fringe paths extend axially a distance f beyond the end of the device 10. From field theory it is known that $$f = 2(b-a) \quad (14)$$

That is, the fringe fields decay axially to negligible levels within a distance approximately equal to twice the separation distance between the electrodes 12 and 14. As shown in FIG. 5B, this distance is constant regardless of immersion depth. In FIG. 5B, the cell 10 has been inserted a distance $\Delta l_1$ further to a depth $l_1$. However, the fringe height f has not changed. It is because these fringe effects do not change that the differential conductance measurement of the invention eliminates the fringe effects from the computation to obtain an accurate electrical conductivity measurement. As long as the cell 10 is not inserted into the liquid so far as to allow the fields to be interfered with by the bottom of the container 32, the fringe effects 60 remain constant with respect to immersion depth.

The total conductance will also include irregular current effects which occur near the surface of the liquid as shown in brackets 61. These surface effects are also independent of immersion depth and are therefore eliminated from the electrical conductivity measurement by the differential computation.

The total impedance measured by the analysis equipment 50 includes the impedance of the leads 38, 40, the impedance of the electrodes and the impedance of the medium between the electrodes. The value of the impedance of the medium can be isolated from the total impedance measurement with the aid of a nulling procedure consisting of measuring the open and short circuit impedances of the electrodes and lead wires.

There are many other means by which the immersion depth of the cell 10 can be varied. For example, the cell 10 can be maintained at a constant height within the medium. The immersion depth is then varied by changing the level of the medium within its container, i.e., by selectively draining or filling the container. Once again, as long as the differential immersion depth is known, the measurement can be obtained.

Figure 6:
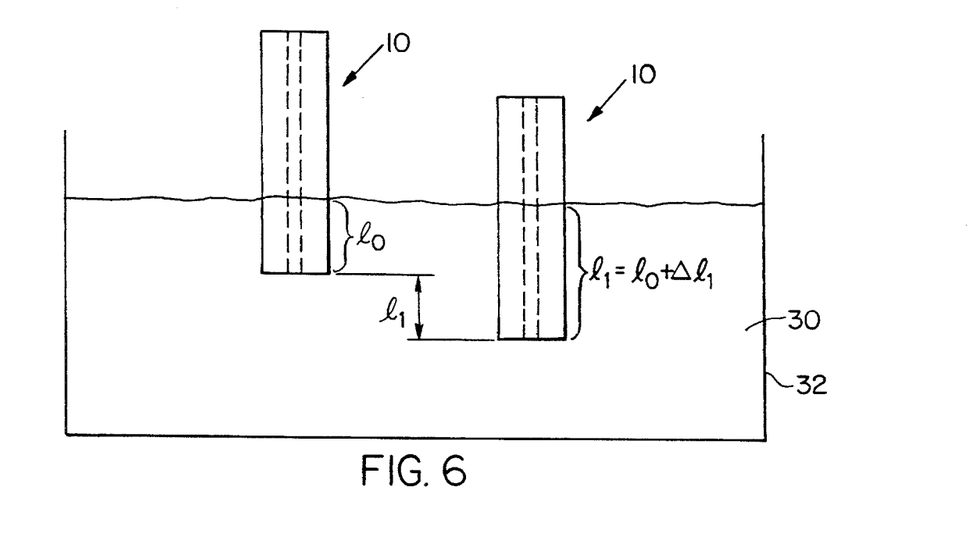
FIG. 6 is a schematic illustration of an alternative embodiment of the invention using multiple cells.

In another embodiment, as shown schematically . In FIG. 6, multiple cells 10 are held in stationary axial positions within the material. Each cell 10 is held at a different immersion depth $l_1$, $l_2$. Alternatively, fully immersed electrodes of different physical length could be used. The conductance $G_1$, $G_2$ measured by each cell 10 provides the differential conductance with respect to immersion depth.

Figure 7:
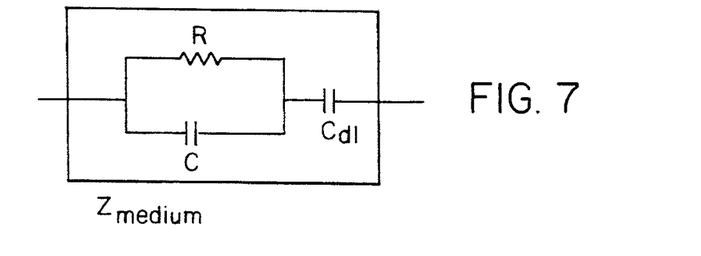
FIG. 7 is an equivalent circuit for the impedance between the electrodes of the device of the invention while immersed in a solution.

FIG. 7 is an equivalent circuit for the impedance between the electrodes of the device 10. A resistance R (conductance G) is in parallel with the capacitance of the medium C. That parallel combination is in series with the capacitance $C_{dl}$ of the double layer at the electrodes. This double-layer capacitance is well known in electrochemistry. In most cases, $C_{dl}$ is much larger than C. An expression for the impedance of the equivalent circuit in FIG. 5 is given by $$Z = \frac{1}{j\omega C_{dl}} + \frac{R \frac{1}{j\omega C}}{R + \frac{1}{j\omega C}}. \tag{15}$$

Figure 8:
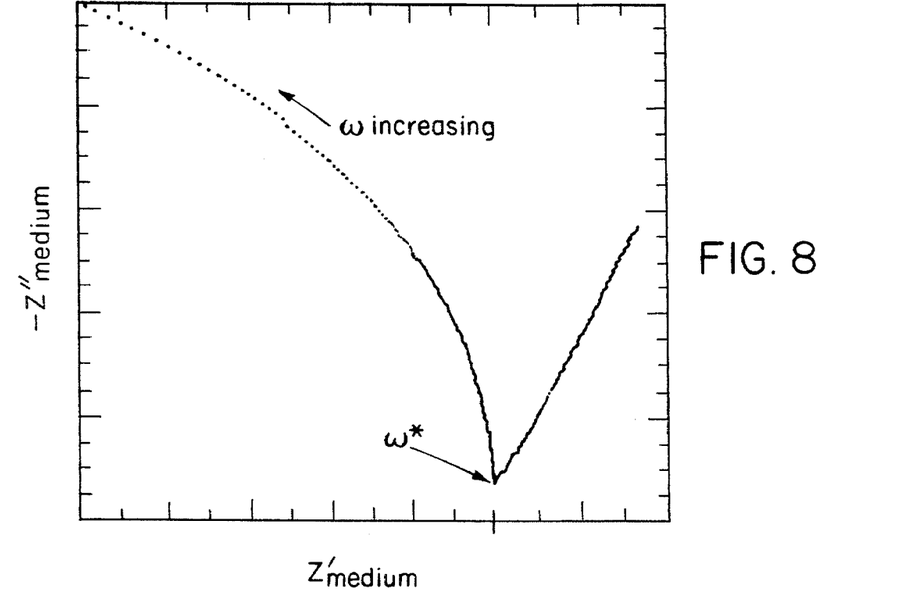
FIG. 8 is a plot in the complex plane of the impedance of a medium between the electrodes of the device of the invention.

To obtain the impedance measurement, the analysis equipment 50 sweeps or steps through a frequency range whose limits are determined by various factors including properties of the leads, electrodes and the medium itself. FIG. 8 is a plot of the impedance of the medium in the complex plane. In FIG. 8, the real part of the impedance Z' is plotted along the horizontal axis and the imaginary part Z" is plotted along the vertical axis. When the full range of frequencies is swept or stepped through and a complete impedance measurement is acquired, the values are analyzed to determine a frequency $\omega^*$ at which the imaginary part of the impedance is a minimum, and, consequently at which the real part is most dominant. At this frequency, the impedance is concluded to most closely approach pure resistance. This impedance is taken to be the total resistance including the resistance between the electrodes and the parallel fringe resistance. Referring to equation 15, at this frequency, the first term is much smaller than the second term and therefore is effectively eliminated. The second term is reduced to R.

This ac spectroscopic analysis is performed at each immersion depth to obtain a value for total resistance R. Each of these R values obtained for each immersion depth is used in subsequent processing to perform the analysis described above in order to compute the electrical conductivity of the medium.

Figure 9:
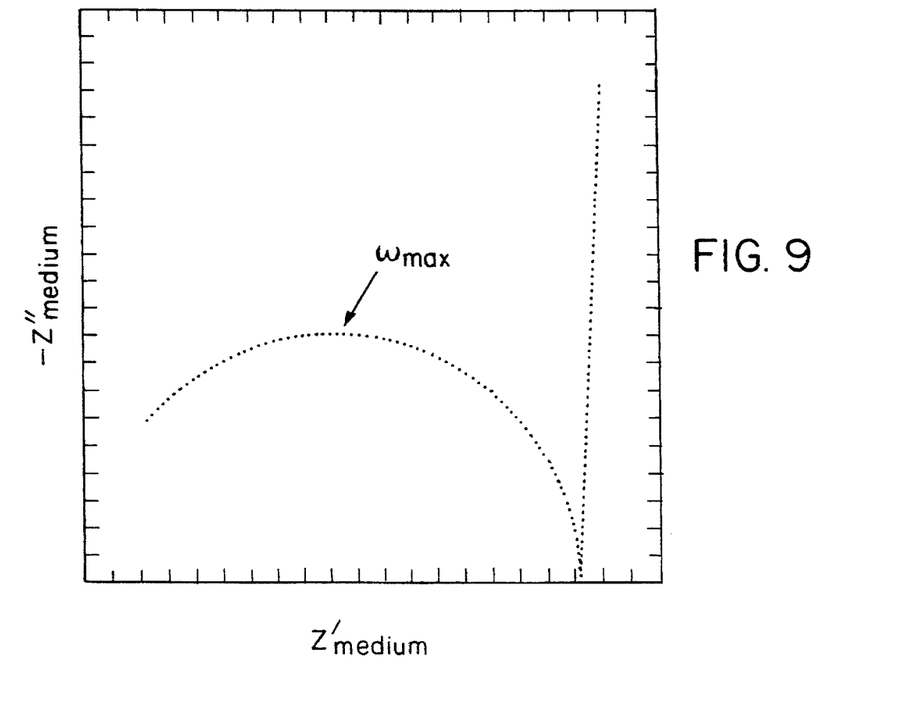
FIG. 9 is a plot in the complex plane of the impedance of a liquid solution between the electrodes of the device of the invention showing a peak in the plot.

The spectroscopic analysis can also be used to determine the dielectric constant $\epsilon$ of the medium. The plot of FIG. 8 can be extended to higher frequencies $\omega$ as shown in FIG. 9 until a local maximum in $-Z"$ with respect to Z' is obtained at a frequency $\omega_{max}$. At that frequency, the magnitude of the resistive impedance Z' is equal to the magnitude of the reactive impedance Z", and the capacitance C can therefore be determined since $$\omega_{max} = \frac{1}{RC}.$$

The relationship between capacitance and dielectric constant is identical to that for conductance and electrical conductivity for all frequencies greater than or equal to $\omega^*$. That is, $$C = \epsilon \left[ \frac{2\pi l}{\ln\left(\frac{b}{a}\right)} \right] + C_{fringe}. \tag{16}$$

Therefore, following the derivation set forth above for conductance and electrical conductivity, equation 13 becomes $$\epsilon = \frac{\ln\left(\frac{b}{a}\right)}{2\pi} \left[ \frac{C_1 - C_0}{\Delta l_1} \right], \tag{17}$$

Thus, capacitance measurements taken over differential immersion depth yield an accurate measured value for dielectric constant of the medium.

It will be understood that this spectroscopic analysis can be performed as an analysis of the complex admittance of the medium between the electrodes, over the appropriate frequency range as noted previously, to allow determination of the complex electrical parameter of the medium (i.e., $\sigma + j\omega\epsilon$) from the differential admittance with respect to depth of immersion.

While this invention has been particularly shown and described with references to preferred embodiments thereof, it will be understood by those skilled in the art that various changes in form and details may be made therein without departing from the spirit and scope of the invention as defined by the appended claims.

The invention claimed is:

1. Electrical parameter measurement apparatus for measuring electrical parameters of a medium comprising:

first and second elongated electrodes for receiving the medium therebetween, the first electrode being within and parallel to the second electrode;

means for varying the depth of the medium between the electrodes, measurements through the electrodes indicative of impedance of the medium being obtained at plural depths; and an analyzer for analyzing the plural measurements to obtain an indication of an electrical parameter from the measurements.

2. Apparatus as claimed in claim 1 wherein the electrical parameter is electrical conductivity of the medium.

3. Apparatus as claimed in claim 1 wherein the electrical parameter is dielectric constant of the medium.

4. Apparatus as claimed in claim 1 wherein the analyzer obtains the indication of an electrical parameter using differential depth.

5. Apparatus as claimed in claim 1 wherein the electrodes are coaxial.

6. Apparatus as claimed in claim 1 wherein the medium is a fluid.

7. Apparatus as claimed in claim 1 wherein the medium is a solid.

8. Apparatus as claimed in claim 1 wherein the medium is a mixture of a fluid and a solid.

9. Apparatus as claimed in claim 1 wherein the electrodes are coaxial cylinders.

10. Apparatus as claimed in claim 1 wherein the means for varying the depth of the medium between the electrodes comprises a support for axially displaying the electrodes within the medium.

11. Apparatus as claimed in claim 1 wherein the means for varying the depth of the medium between the electrodes comprises a support for maintaining the electrodes in a stationary axial position while varying a level of the medium.

12. Apparatus as claimed in claim 1 wherein the means for varying the depth of the medium between the electrodes comprises a support for maintaining a plurality of pairs of electrodes in stationary axial positions at different depths within the medium.

13. Apparatus as claimed in claim 1 wherein the means for varying the depth of the medium between the electrodes comprises a support for maintaining a plurality of pairs of electrodes of different lengths fully immersed within the medium.

14. A method of measuring electrical parameters of media comprising:

at least partially filling a space between first and second elongated electrodes with a medium through a range of depths, the first electrode being within and parallel to the second electrode;

obtaining a measurement indicative of impedance of the medium at each of plural depths; and analyzing the plural measurements to obtain an indication of an electrical parameter using differential depth.

15. The method of claim 14 wherein at least partially filling the space between the electrodes through a range of depths comprises axially displacing the electrodes into the medium.

16. The method of claim 14 wherein at least partially filling the space between the electrodes through a range of depths comprises supporting the electrodes in a stationary axial position while varying a level of the medium.

17. The method of claim 14 wherein at least partially filling the space between the electrodes through a range of depths comprises supporting plural pairs of electrodes in stationary axial positions at different depths within the medium.

18. The method of claim 14 wherein at least partially filling the space between the electrodes through a range of depths comprises supporting plural pairs of electrodes of different lengths fully immersed within the medium.

19. The method of claim 14 wherein the electrical parameter is electrical conductivity of the medium.

20. The method of claim 14 wherein the electrical parameter is dielectric constant of the medium.

21. The method of claim 14 wherein the medium is a fluid.

22. The method of claim 14 wherein the medium is a solid.

23. The method of claim 14 wherein the medium is a mixture of a fluid and a solid.

24. Apparatus as claimed in claim 1 wherein the analyzer generates a relationship between conductance at plural depths and differential depth.

25. Apparatus as claimed in claim 1 wherein, at each depth, measurements indicative of the impedance of the medium are obtained at plural frequencies and a measurement indicative of the conductance of the medium is selected at the frequency at which the reactive component of the measured impedance is a minimum.

26. Apparatus as claimed in claim 1 wherein the analyzer senses a non-linear variation in conductance with respect to depth to identify inaccurate measurements.

27. The method of claim 14 wherein the electrodes are coaxial.

28. The method of claim 14 wherein the electrodes are coaxial cylinders.

29. The method of claim 14 further comprising generating a relationship between conductance at plural depths and differential depth.

30. The method of claim 14 wherein the obtaining step comprises, at each depth:

sensing impedance across the electrodes at plural frequencies; and selecting the impedance measurement at the frequency at which the reactive component of the impedance is a minimum.

31. The method of claim 14 further comprising sensing a non-linear variation in conductance with respect to depth to identify inaccurate measurements.

\* \* \* \* \*